(12) United States Patent
Ham

(10) Patent No.: US 6,334,868 B1
(45) Date of Patent: *Jan. 1, 2002

(54) STENT COVER

(75) Inventor: Kevin Ham, Santa Clara, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/413,317

(22) Filed: Oct. 8, 1999

(51) Int. Cl.$^7$ ................................................ A61F 2/06
(52) U.S. Cl. ...................................................... 623/1.13
(58) Field of Search ................. 623/1.13, 1.1, 623/1.12, 1.23, 1.36; 606/191, 195, 198

(56) References Cited

U.S. PATENT DOCUMENTS

| | | |
|---|---|---|
| 3,839,742 A | 10/1974 | Schwarcz |
| 4,346,028 A | 8/1982 | Griffith |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,816,339 A | 3/1989 | Tu et al. |
| 4,877,030 A | 10/1989 | Beck et al. |
| 4,878,906 A | 11/1989 | Lindemann et al. |
| 4,879,135 A | 11/1989 | Greco et al. |
| 4,994,298 A | 2/1991 | Yasuda |
| 5,019,090 A | 5/1991 | Pinchuk |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,108,755 A | 4/1992 | Daniels et al. |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,192,311 A | 3/1993 | King et al. |

(List continued on next page.)

FOREIGN PATENT DOCUMENTS

| | | |
|---|---|---|
| DE | A-44 07 079 | 9/1994 |
| EP | A-0-604 022 | 1/1994 |
| EP | A-0 578 998 | 6/1994 |
| EP | A-0 621 017 | 10/1994 |
| WO | WO 91/17789 | 11/1991 |
| WO | WO 93/06792 | 4/1993 |
| WO | A-95 29647 | 11/1995 |

OTHER PUBLICATIONS

"IEEE Transactions on Biomedical Engineering," BME–27, No. 11, Nov. 1980.

(List continued on next page.)

Primary Examiner—Kevin Truong
(74) Attorney, Agent, or Firm—Fulwider Patton Lee & Utecht, LLP

(57) ABSTRACT

A stent cover of elastic material having a very precisely defined pattern of elongated perforations formed therein so as to control the expansion of the stent to a preselected shape. Once in place and expanded, the cover additionally prevents the prolapse of lumen wall tissue as well as the escape of embolic materials. The pattern of perforations opens into a pattern of openings that promote the proliferation of endothelial tissue and hence the healing of the lumen at the deployment site.

14 Claims, 2 Drawing Sheets

U.S. PATENT DOCUMENTS

| | | |
|---|---|---|
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,330,550 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,383,928 A | 1/1995 | Scott et al. |
| 5,389,106 A | 2/1995 | Tower |
| 5,441,515 A | 8/1995 | Khosravi et al. |
| 5,584,876 A | 12/1996 | Bruchman et al. |
| 5,591,195 A | 1/1997 | Taheri et al. |
| 5,591,224 A | 1/1997 | Schwartz et al. |
| 5,591,226 A | 1/1997 | Trerotola et al. |
| 5,599,352 A | 2/1997 | Dinh et al. |
| 5,607,464 A | 3/1997 | Trescony et al. |
| 5,607,468 A | 3/1997 | Rogers et al. |
| 5,607,478 A | 3/1997 | Lentz et al. |
| 5,609,624 A | 3/1997 | Kalis |
| 5,609,626 A | 3/1997 | Quijano et al. |
| 5,609,629 A | 3/1997 | Fearnot et al. |
| 5,624,411 A | 4/1997 | Tuch |
| 5,628,781 A | 5/1997 | Williams et al. |
| 5,628,782 A | 5/1997 | Myers et al. |
| 5,628,785 A | 5/1997 | Schwartz et al. |
| 5,628,786 A | 5/1997 | Banas et al. |
| 5,628,787 A | 5/1997 | Mayer |
| 5,628,788 A | 5/1997 | Pinchuk |
| 5,629,077 A | 5/1997 | Turnlund et al. |
| 5,630,840 A | 5/1997 | Mayer |
| 5,632,776 A | 5/1997 | Kurumatani et al. |
| 5,632,779 A | 5/1997 | Davidson |
| 5,632,840 A | 5/1997 | Campbell |
| 5,637,113 A * | 6/1997 | Tartaglia et al. ............ 606/194 |
| 5,645,559 A | 7/1997 | Hachtman et al. |
| 5,653,745 A | 8/1997 | Trescony et al. |
| 5,653,746 A | 8/1997 | Schmitt |
| 5,653,747 A | 8/1997 | Dereume |
| 5,665,077 A | 9/1997 | Rosen et al. |
| 5,665,114 A | 9/1997 | Weadock et al. |
| 5,667,523 A | 9/1997 | Bynon et al. |
| 5,674,241 A | 10/1997 | Bley et al. |
| 5,674,277 A | 10/1997 | Freitag |
| 5,679,400 A | 10/1997 | Tuch |
| 5,681,345 A | 10/1997 | Euteneuer |
| 5,683,448 A | 11/1997 | Cragg |
| 5,683,453 A * | 11/1997 | Palmaz ...................... 623/1.13 |
| 5,693,085 A | 12/1997 | Buirge et al. |
| 5,697,967 A | 12/1997 | Dinh et al. |
| 5,700,285 A | 12/1997 | Myers et al. |
| 5,711,763 A | 1/1998 | Nonami et al. |
| 5,713,949 A | 2/1998 | Jayaraman |
| 5,716,394 A | 2/1998 | Bruchman et al. |
| 5,716,395 A | 2/1998 | Myers et al. |
| 5,716,660 A | 2/1998 | Weadock et al. |
| 5,723,003 A | 3/1998 | Winston et al. |
| 5,723,004 A | 3/1998 | Dereume et al. |
| 5,725,547 A | 3/1998 | Chuter |
| 5,735,892 A | 4/1998 | Myers et al. |
| 5,749,880 A | 5/1998 | Banas et al. |
| 5,749,922 A | 5/1998 | Slepian et al. |
| 5,755,774 A | 5/1998 | Pinchuk |
| 5,755,778 A | 5/1998 | Kleshinski |
| 5,776,184 A | 7/1998 | Tuch |
| 5,779,729 A | 7/1998 | Severini |
| 5,779,732 A | 7/1998 | Amundson |
| 5,782,904 A | 7/1998 | White et al. |
| 5,782,908 A | 7/1998 | Cahalan et al. |
| 5,788,626 A | 8/1998 | Thompson |
| 5,800,511 A | 9/1998 | Mayer |
| 5,810,870 A | 9/1998 | Myers et al. |
| 5,814,063 A | 9/1998 | Freitag |
| 5,824,037 A | 10/1998 | Fogarty et al. |
| 5,824,046 A | 10/1998 | Smith et al. |
| 5,824,049 A | 10/1998 | Ragheb et al. |
| 5,836,962 A | 11/1998 | Gianotti |
| 5,843,089 A | 12/1998 | Sahatjian et al. |
| 5,851,232 A | 12/1998 | Lois |
| 5,895,407 A | 4/1999 | Jayaraman |
| 5,928,279 A | 7/1999 | Shannon et al. |
| 5,951,586 A | 9/1999 | Berg et al. |
| 5,957,974 A | 9/1999 | Thompson et al. |
| 5,961,545 A | 10/1999 | Lentz et al. |

OTHER PUBLICATIONS

"Glow Discharge Polymers as Coatings for Implanted Devices," by Allen W. Hahn, et al., printed by John M. Dalton Research Center, University of Missouri (1981).

"Biocompatibility of Glow–Discharge–Polymerized Films and Vacuum–Deposited Parylene," by Allen W. Hahn, et al., published by John M. Dalton Research Center, University of Missouri (1984).

"Fiber–Reinforced Absorbable Composite for Orthopedic Surgery," by R.A. Casper, B.S. Kelley, R.L. Dunn, A.G. Potter and D.N.Ellis in *Polymeric Materials Science and Engineering*,Proceedings of the ACS Division of Polymeric Materials: Science and Engineering, vol. 53, Fall Meeting 1985.

"Totally Resorbable High–Strength Composite Material," by Benjamin S. Kelley, Richard L. Dunn and Robert A. Casper, *Advances in Biomedical Polymers,* Edited by Charles G. Gebelein (1987).

"Electrical Insulation of Implantable Devices by Composite Polymer Coatings," by M.F. Nichols and A.W. Hahn published by John M. Dalton Research Center, University of Missouri, as Paper No. 87–0110 (1987).

"Long–Term implants of Parylene–C Coated Microelectrodes," by E.M. Schmidt, J.S. McIntosh and M.J. Bak, in *Medical & Biological Engineering & Computing,* Jan. 1988.

"Parylene, a Biostable Coating for Medical Applications," by Roger Olson, for NOVA TRAN Parylene Coating Services (Jul. 25, 1988, Nov. 14, 1988).

"A view of Vascular Stents," by Richard A. Schatz, M.D. from the Arizona Heart Institute Foundation, Phoenix, Arizona (1988).

"Advances in Coronary Angioplasty: Endovascular Stents," by David W.M. Muller and Stephen G. Ellis, M.D. in *Coronary Artery Disease,* Jul./Aug. 1990, vol. 1, No. 4.

"An Update on Coronary Stents," by Shink–Chiu Wong, M.D. and Richard A. Schatz, M.D. in *Cardio,* Feb. 1992.

"Parylene Coatings for Medical Applications," by Victor A. Bull, in *Medical Product Manufacturing News,* Mar. 1993.

"Information Regarding Parylene C Coating for ACS Metal Stent," In–House Memorandum from Ed Newton to Joe Callol, Mike Clayman, Dennis Houlsby and Joe Tartaglia, dated Oct. 15, 1993 attaching "Parylene, a Biostable Coating for Medical Applications," by Roger Olson.

Brochure entitled "Parylene Conformal Coating" by NOVA TRAN Custom Coating Services, a Subsidiary of Union Carbide Corporation (Undated).

* cited by examiner

STENT COVER

BACKGROUND OF THE INVENTION

The present invention generally relates to intravascular stents and more particularly pertains to covers that permanently envelop the stent's supporting structure.

Stents or expandable grafts are implanted in a variety of body lumens in an effort to maintain patency. These devices are typically intraluminally implanted by use of a catheter which is inserted at an easily accessible location and then advanced through the vasculature to the deployment site. The stent is initially maintained in a radially compressed or collapsed state to enable it to be maneuvered through the body lumen. Once in position, the stent is deployed which, depending on its construction, is achieved either automatically by for example the removal of a restraint or actively by for example the inflation of a balloon about which the stent is carried on the catheter.

Various stent configurations are well known and typically comprise a generally tubular arrangement of struts, spines, wires, etc. Such elements are advantageously positioned, oriented and interlinked to enable the stent to be expanded and to then provide the required radial support to lumen walls in which they are deployed. The particular stent configuration that is employed along with the material or materials selected for its construction determine the performance characteristics of the resulting device. Such characteristics include, but are not limited to, radial stiffness, longitudinal flexibility, longitudinal stability upon expansion, expansion ratio, coverage area, etc. Most stent configurations that are presently known have a fairly open structure with a commensurately limited coverage area. As a stent is expanded, a given area of support structure becomes distributed over an even greater area. This is especially aggravated in the event the stent configuration is selected so as to maintain a constant length during expansion.

The voids between the various support elements can be problematic. For example, lumen wall tissue directly adjacent to such voids is not supported and can prolapse. Similarly, plaque or other material not directly supported by a stent element could also prolapse or come loose and be swept downstream to cause an embolism. As a result, it is usually most desirable for a stent to provide as much coverage as possible.

Another problem encountered with heretofore known stent configurations is the risk of over-expanding the stent so as to unnecessarily traumatize or otherwise distort the body lumen at the deployment site. While a particular stent configuration may inherently limit the maximum diameter that can be achieved, such maximum can nonetheless exceed the maximum diameter that can be tolerated by the body lumen at the deployment site. Additionally, it may be desirable for certain portions of the stent to expand to a greater diameter than other portions of the stent. Conversely, it may be desirable for the stent to achieve a constant diameter over its entire length in contrast to the natural "bow-tie" effect many configurations are prone to as a stent's resistance to expansion near its ends is often less than near its center and due to expansion characteristics of inflatable balloons at the balloon tapers.

SUMMARY OF THE INVENTION

The stent cover of the present invention overcomes the shortcomings of previously known covers. More specifically, the stent cover can be easily tailored to the unique requirements of a particular application. Such cover then serves to limit the expansion of the stent to either a preselected constant diameter or a preselected shape of varying diameter. Upon deployment of the stent with the cover in place, the prolapse of lumen wall tissue or plaque is positively precluded as is the escape of any embolic materials. Thus, the cover of the present invention is especially well suited for use in carotid artery applications. The healing of the deployment site is nonetheless not compromised as the cover of the present invention promotes the proliferation of endothelial tissue.

The cover of the present invention achieves the above-described advantages in that an elastomeric material is employed having very precisely defined pattern of elongated perforations or slits formed therein. The number, lengths and distribution of such perforations dictate the expansion characteristics of the material which in turn controls the ultimate expansion of the stent. Sections of the cover having an increased density of perforations or having perforations of longer length offer a reduced resistance to expansion while sections of low perforation density or shorter perforations more effectively resist expansion. Upon expansion, the perforations open into holes or orifices that promote the proliferation and ingrowth of endothelial tissue.

By selecting a perforation configuration other than what is essentially a one-dimensional slit, the stresses developed within the cover material upon expansion can be significantly reduced to preclude tearing. Additionally, by controlling the size and shape of the initially formed perforation, a more advantageously shaped and sized orifice is attainable upon expansion.

The stent cover of the present invention is manufactured either by perforating a tube of elastomeric material or by perforating a flat sheet of the material prior to forming it into a tubular configuration. The perforations may be formed by mechanical means or by laser cutting. By advantageously folding the material, multiple perforations are formed simultaneously. Cutting the material while in an expanded state allows more precisely defined openings to be formed.

These and other features and advantages of the present invention will become apparent from the following detailed description of a preferred embodiment which, taken in conjunction with the accompanying drawings, illustrates by way of example the principles of the invention.

DETAILED DESCRIPTION OF THE PREFERRED EMBODIMENTS

The cover of the present invention is positioned about a stent prior to its deployment. Such cover includes a pattern of perforations formed therein that is precisely tailored for a particular application. Once in place about the stent, the stent is maneuvered to the deployment site and expanded in the conventional manner. The cover remains permanently in place about the deployed stent to prevent tissue or plaque prolapse and the escape of embolic materials without significantly interfering in the ingrowth and proliferation of endothelial tissue.

Figure 1:
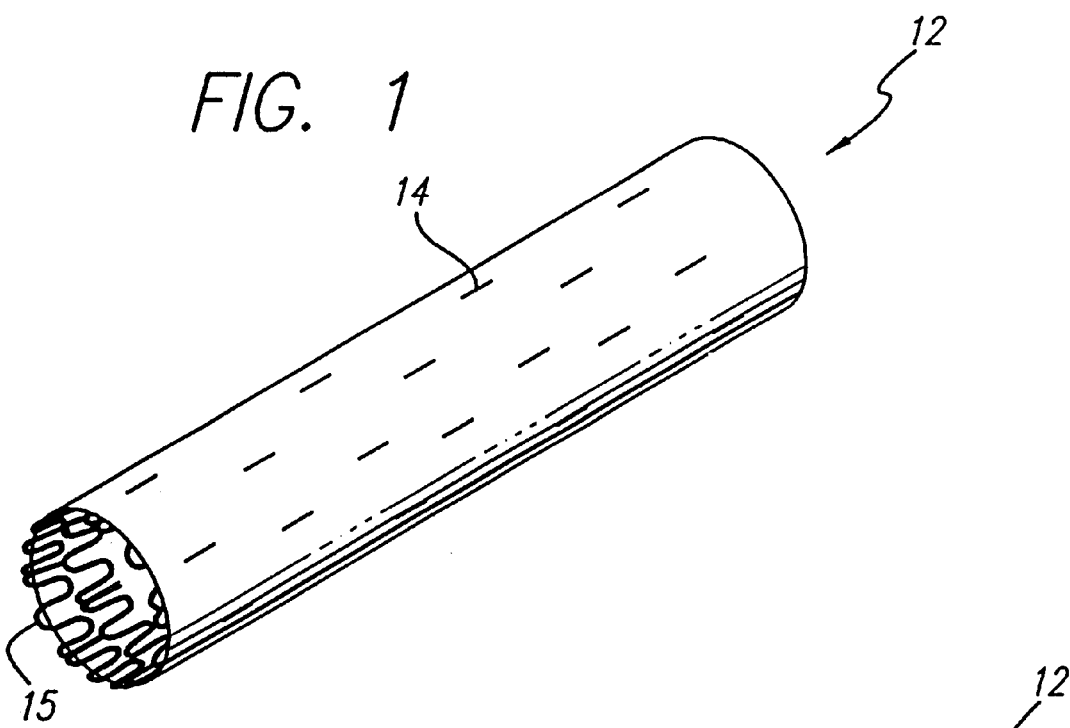
FIG. 1 is a perspective view of a cover of the present invention in place about an unexpanded stent.

As shown in FIG. 1, stent cover 12 of the present invention has a pattern of fine perforations in the form of substantially one dimensional slits 14 extending across the cover's entire surface. In this particular embodiment, the slits are distributed in a substantially uniform pattern across the entire surface area of the stent cover. It is to be additionally noted that the slits are each arranged in a substantially longitudinal orientation. The use of the cover is not limited to any particular type of stent nor to any particular method of deployment nor for any particular application. The stent cover is stretched tightly over stent 15 and is intended to cover some or all of the stent. It may be desirable to have the cover overlay only a portion of the stent so that the exposed stent portions can embed in the vessel wall to more firmly implant the stent.

Figure 2:
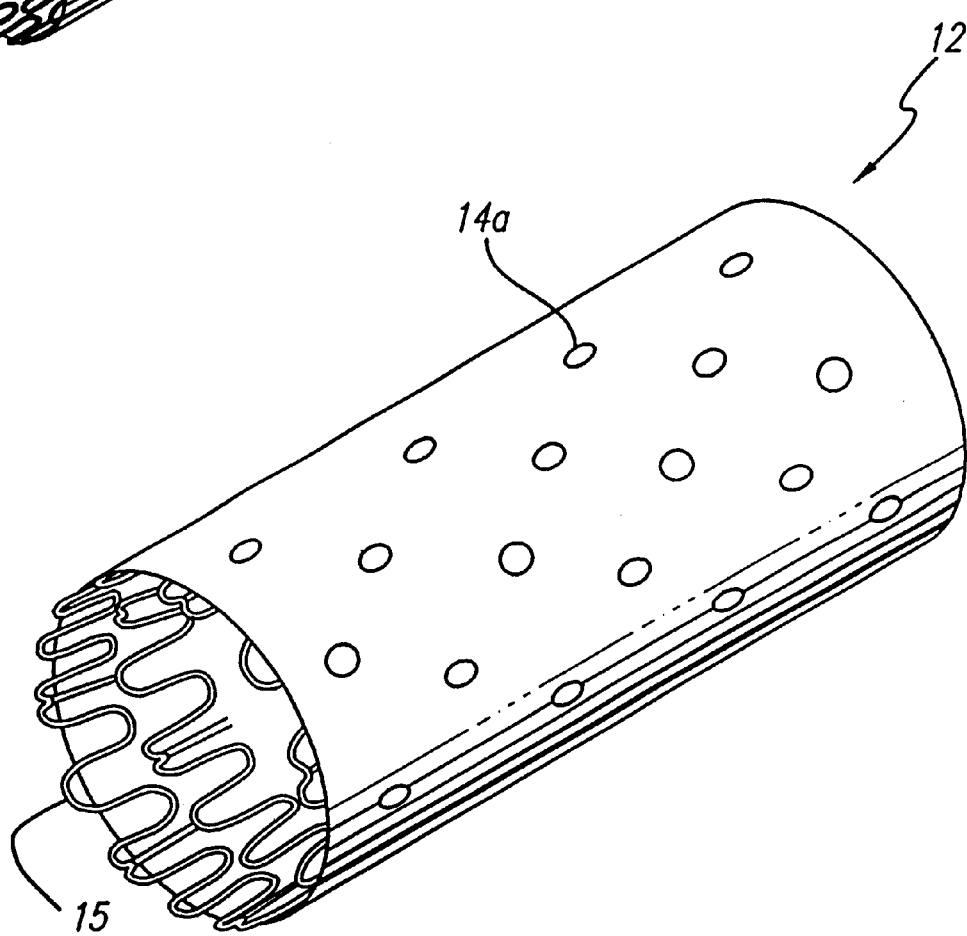
FIG. 2 is a perspective view of the cover shown in FIG. 1 upon expansion of the underlying stent.

The stent cover shown in FIG. 1 is shown in an expanded condition in FIG. 2. Each of the slits has assumed a generally oval configuration 14a as is the natural result of stretching a material initially having a straight perforation of constant width formed therein.

Figure 3:
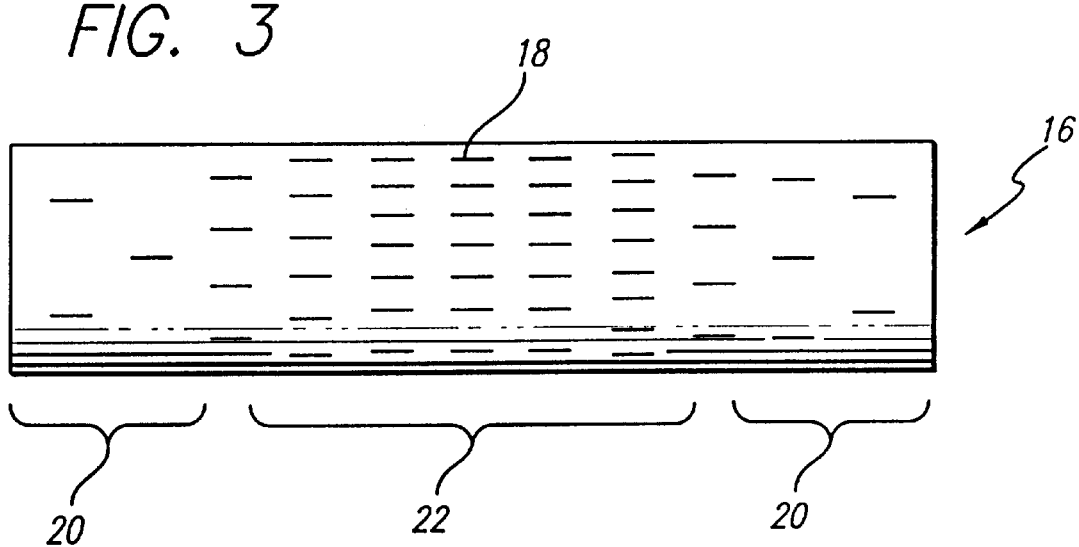
FIG. 3 is a side plan view of a cover of the present invention with an alternative embodiment pattern of slits.

As shown in FIG. 3, an alternative embodiment stent cover 16 utilizes a varying pattern of slits 18. Each slit is of the same length, but the density of slits varies along the length of the stent. In this particular embodiment, the density of slits is much lower in the regions 20 near the ends of the stent than in its central region 22. As a result, upon expansion, the cover will offer greater resistance to radial expansion near the ends than in the central region of the stent. This has the advantageous effect of offsetting the "bow-tie" effect that many stent configurations are prone to due to the natural drop-off of strength near the stent ends. The bow-tie effect also can be caused by the ends of the balloon on a balloon catheter (not shown) expanding before the central part of the balloon. Typically, the balloon ends are tapered and weaker than the central part of the balloon, and therefore have a tendency to expand before the central part of the balloon. This in turn causes the stent ends to flare outwardly giving the stent a "bow-tie" or "dog-bone" appearance. By supplementing a stent's resistance to radial deformation with the resistance afforded by the cover, the shape of the expanded stent structure can be tailored to any desired configuration. By gradually increasing the slit density as the center is approached to mimic the gradual curvature of the bow-tie shape a particular stent configuration is inclined to assume, such stent will instead assume an expanded cylindrical shape. Conversely, by varying the slit density distribution in order to cause the expanded stent structure to assume a cylindrical shape that varies along its length, the natural shape of a particular lumen at a particular lumen site can be duplicated.

Figure 4:
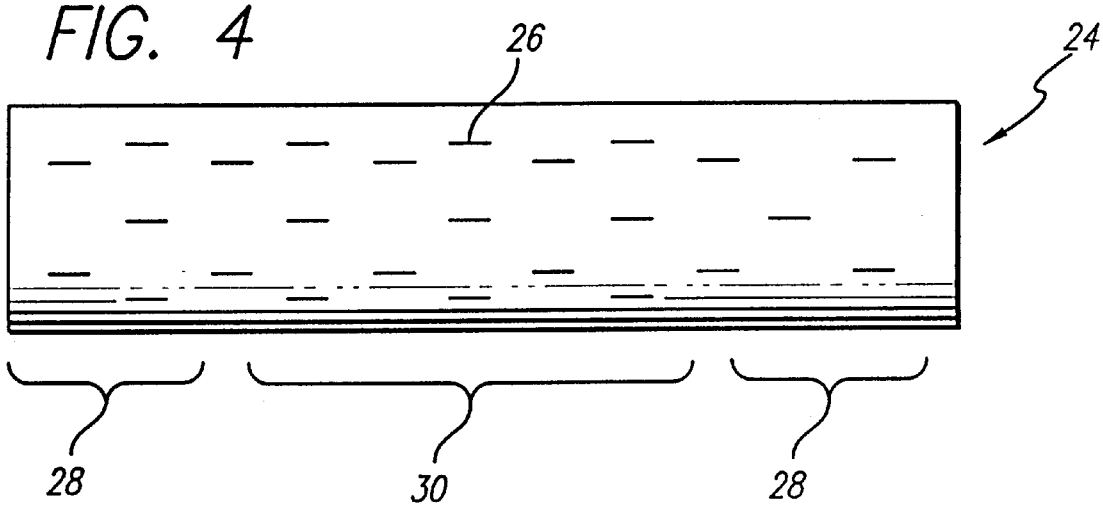
FIG. 4 is a side plan view of a cover of the present invention with another alternative embodiment pattern of slits.

FIG. 4 illustrates another alternative stent cover 24 embodiment intended to offset a stent's natural tendency to assume a "bow-tie" shape. Rather than varying the density of the slit pattern, the length of the slits 26 is varied such that the slits in the end regions 28 of the stent cover are shorter than in the central region 30. Longer slits will weaken the ability of the cover to resist expansion so that the pattern will tend to offset an underlying stent's natural tendency to assume a bow-tie shape. Similar to the previously described embodiment, a gradual change in the length of the slits rather than an abrupt change will net an expanded configuration of a more constant cylindrical shape.

Figure 5A:
FIGS. 5a and 5b are top plan views of an alternative embodiment opening shape before and after expansion.
Figure 5B:
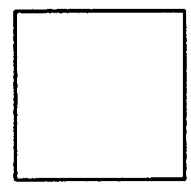

While the above described embodiments employ slits of constant width to yield substantially oval or circular openings upon expansion, forming a perforation in the material to yield a shape as is shown in FIG. 5a would yield a substantially square or rectangular opening shown in FIG. 5b upon expansion. This has the effect of reducing the stresses the cover material would otherwise be subjected to near the ends of the slits and thereby reduces the risk of tearing. For example, C-Flex is a highly elastic material suitable for the cover of the invention and can be obtained from Consolidated Polymer Technologies, Largo, Fla.

The material employed for the construction of the cover of the present invention may include any of the thin, elastic and biocompatible polymers well known in the art. The diameter of the tubular structure formed therewith while in its unexpanded state is selected to be slightly less than the diameter of the stent in its unexpanded state so as to automatically grip and adhere to the stent upon fitment thereabout. The slits or any of the other selected perforations shapes may be formed in the cover material while in an unexpanded state or while in an expanded state. Much smaller openings are achievable if the cuts are made while the cover material is in an expanded state. The process may also be expedited by folding the cover material one or more times such that a single cut will extend through multiple layers. Cutting may be accomplished through mechanical means or by laser.

While a particular form of the invention has been illustrated and described, it will also be apparent to those skilled in the art that various modifications can be made without departing from the spirit and scope of the invention. More specifically, the cover of the present invention is not limited for us with any particular type of stent configuration or for any particular type of application. Moreover, the underlying stent may be expanded by any number of well known techniques. Accordingly, it is not intended that the invention be limited except by the appended claims.

What is claimed:

1. A stent cover, comprising:
   a tubular section of elastomeric material for covering an unexpanded stent wherein such tubular section is dimensioned and has an elasticity selected so as to constrain the expansion of such stent, and wherein a pattern of perforations formed in said tubular section is selected to modify the elasticity of the section and thereby constrain the expansion of the underlying stent to a preselected configuration along its length.

2. The stent cover of claim 1, wherein the pattern perforations are arranged in a longitudinal orientation.

3. The stent cover of claim 1, wherein the pattern of perforations is uniform.

4. The stent cover of claim 1, wherein the pattern of perforations is non-uniform.

5. The stent cover of claim 4, wherein the density of the pattern of perforations varies along the length of the cover.

6. The stent cover of claim 5, wherein the density of said pattern of perforations is greater near the center of said cover than near the ends.

7. The stent cover of claim 1, wherein the perforations are elongated.

8. The stent cover of claim 4, wherein the lengths of the perforations varies along the length of the cover.

9. The stent cover of claim 8, wherein the perforations are longer near the center of the cover than near the ends.

10. The stent cover of claim 5, wherein the lengths of the perforations vary over the length of the cover.

11. The stent cover of claim 10, wherein the density and lengths of the perforations are greater near the center of the cover than near the ends.

12. The stent cover of claim 1, wherein the perforations are of constant width while the stent cover is in an unexpanded state.

13. The stent cover of claim 1, wherein the width of the perforations varies along the length of the perforations while the cover is in an unexpanded state.

14. The stent cover of claim 13, wherein the width of the perforations is configured to achieve a substantially rectangular shape upon expansion.

* * * * *